(12) United States Patent
Bown et al.

(10) Patent No.: US 8,758,268 B2
(45) Date of Patent: Jun. 24, 2014

(54) SHAPE MEMORY MEDICAL DEVICE AND METHODS OF USE

(75) Inventors: Matthew W. Bown, West Bountiful, UT (US); David M. Butts, Riverton, UT (US)

(73) Assignee: C. R. Bard, Inc., Murray Hill, NJ (US)

(*) Notice: Subject to any disclaimer, the term of this patent is extended or adjusted under 35 U.S.C. 154(b) by 1834 days.

(21) Appl. No.: 12/028,555

(22) Filed: Feb. 8, 2008

(65) Prior Publication Data
US 2008/0194994 A1    Aug. 14, 2008

Related U.S. Application Data

(60) Provisional application No. 60/900,202, filed on Feb. 8, 2007.

(51) Int. Cl.
*A61B 5/00* (2006.01)
(52) U.S. Cl.
USPC .......................................... 600/585; 148/563
(58) Field of Classification Search
USPC .......................................... 600/585; 148/563
See application file for complete search history.

(56) References Cited

U.S. PATENT DOCUMENTS

| | | | |
|---|---|---|---|
| 3,827,426 A | 8/1974 | Page et al. | |
| 4,283,233 A | 8/1981 | Goldstein et al. | |
| 4,335,571 A | 6/1982 | Tarantola | |
| 4,352,542 A | 10/1982 | Tydings | |
| 4,484,955 A | 11/1984 | Hochstein | |
| 4,665,906 A | 5/1987 | Jervis | |
| 4,934,380 A | 6/1990 | de Toledo | |
| 5,060,660 A | 10/1991 | Gambale et al. | |
| 5,069,226 A * | 12/1991 | Yamauchi et al. | 600/585 |
| 5,171,383 A | 12/1992 | Sagae et al. | |
| 5,211,183 A | 5/1993 | Wilson | |

(Continued)

FOREIGN PATENT DOCUMENTS

| | | |
|---|---|---|
| CN | 102427844 A | 4/2012 |
| EP | 860177 A1 | 8/1998 |

(Continued)

OTHER PUBLICATIONS

PCT Notification of Transmittal of the International Search Report and the Written Opinion of the International Searching Authority.

(Continued)

*Primary Examiner* — Max Hindenburg
*Assistant Examiner* — Renee Danega
(74) *Attorney, Agent, or Firm* — Rutan & Tucker, LLP (57) ABSTRACT

A shaped guidewire for use in medical applications is disclosed. The guidewire is shaped so as to prevent inadvertent advancement of the guidewire into the corpus of a patient during use. In one embodiment, the guidewire includes an elongate body that defines proximal and distal ends. The guidewire body further defines a shaped portion that is positioned intermediate the proximal and distal ends. The shaped portion of the guidewire is at least partially composed of a shape memory material, such as nitinol, and is deflected from a longitudinal axis defined by an undeflected portion of the guidewire body. The shaped portion is disposed in one embodiment at the proximal end of the guidewire. In another embodiment, a proximal portion of the nitinol guidewire can be treated to impart malleability and enable deflection by a clinician. Methods for forming the shaped or malleable guidewire to include a deflected portion are disclosed.

20 Claims, 6 Drawing Sheets

(56) References Cited

U.S. PATENT DOCUMENTS

| | | | |
|---|---|---|---|
| 5,238,004 A | 8/1993 | Sahatjian et al. | |
| 5,299,580 A | 4/1994 | Atkinson et al. | |
| 5,341,818 A | 8/1994 | Abrams et al. | |
| 5,365,943 A | 11/1994 | Jansen | |
| 5,368,049 A | 11/1994 | Raman et al. | |
| 5,383,467 A | 1/1995 | Auer et al. | |
| 5,437,288 A | 8/1995 | Schwartz et al. | |
| 5,452,726 A * | 9/1995 | Burmeister et al. | 600/585 |
| 5,643,281 A | 7/1997 | Suhocki et al. | |
| 5,656,029 A | 8/1997 | Imran et al. | |
| 5,690,120 A | 11/1997 | Jacobsen et al. | |
| 5,827,241 A * | 10/1998 | Douk et al. | 604/523 |
| 5,830,156 A * | 11/1998 | Ali | 600/585 |
| 5,843,050 A | 12/1998 | Jones et al. | |
| 5,865,721 A | 2/1999 | Andrews et al. | |
| 5,876,356 A | 3/1999 | Viera et al. | |
| 5,935,108 A | 8/1999 | Katoh et al. | |
| 6,004,279 A | 12/1999 | Crowley et al. | |
| RE36,628 E | 3/2000 | Sagae et al. | |
| 6,106,642 A | 8/2000 | DiCarlo et al. | |
| 6,238,404 B1 | 5/2001 | Hidalgo et al. | |
| 6,240,727 B1 | 6/2001 | Goldstein et al. | |
| 6,254,550 B1 * | 7/2001 | McNamara et al. | 600/585 |
| 6,352,515 B1 | 3/2002 | Anderson et al. | |
| 6,355,016 B1 | 3/2002 | Bagaoisan et al. | |
| 6,425,887 B1 | 7/2002 | McGuckin et al. | |
| 6,440,088 B1 | 8/2002 | Jacobsen et al. | |
| 6,464,650 B2 | 10/2002 | Jafari et al. | |
| 6,517,481 B2 | 2/2003 | Hoek et al. | |
| 6,572,608 B1 | 6/2003 | Lee et al. | |
| 6,592,559 B1 | 7/2003 | Pakter et al. | |
| 6,592,570 B2 | 7/2003 | Abrams et al. | |
| 6,669,670 B1 | 12/2003 | Muni et al. | |
| 6,673,025 B1 | 1/2004 | Richardson et al. | |
| 6,682,493 B2 | 1/2004 | Mirigian | |
| 6,761,696 B1 | 7/2004 | Wong | |
| 6,939,361 B1 | 9/2005 | Kleshinski | |
| 7,237,313 B2 | 7/2007 | Skujins et al. | |
| 7,670,302 B2 | 3/2010 | Griffin et al. | |
| 2003/0069522 A1 | 4/2003 | Jacobsen et al. | |
| 2003/0216668 A1 | 11/2003 | Howland et al. | |
| 2004/0093017 A1 | 5/2004 | Chanduszko | |
| 2004/0129352 A1 * | 7/2004 | Shiota | 148/527 |
| 2004/0168752 A1 * | 9/2004 | Julien | 148/563 |
| 2004/0181174 A2 * | 9/2004 | Davis et al. | 600/585 |
| 2004/0199088 A1 | 10/2004 | Bakos et al. | |
| 2004/0243095 A1 | 12/2004 | Nimkar et al. | |
| 2005/0054950 A1 * | 3/2005 | Parins | 600/585 |
| 2005/0054953 A1 * | 3/2005 | Ryan et al. | 600/585 |
| 2005/0113862 A1 * | 5/2005 | Besselink et al. | 606/200 |
| 2005/0145307 A1 | 7/2005 | Shireman et al. | |
| 2006/0047223 A1 | 3/2006 | Grandfield et al. | |
| 2006/0106407 A1 * | 5/2006 | McGuckin et al. | 606/159 |
| 2007/0032746 A1 | 2/2007 | Sell | |
| 2007/0073387 A1 | 3/2007 | Forster et al. | |
| 2007/0088254 A1 | 4/2007 | DeStefano | |
| 2007/0100285 A1 | 5/2007 | Griffin et al. | |
| 2007/0112282 A1 | 5/2007 | Skujins et al. | |
| 2007/0123805 A1 | 5/2007 | Shireman et al. | |
| 2007/0213689 A1 | 9/2007 | Grewe et al. | |
| 2007/0244413 A1 | 10/2007 | Biggins | |
| 2007/0244550 A1 * | 10/2007 | Eidenschink | 623/1.49 |
| 2008/0064988 A1 | 3/2008 | Carter et al. | |
| 2010/0249655 A1 | 9/2010 | Lemon | |
| 2011/0257592 A1 | 10/2011 | Ventura et al. | |

FOREIGN PATENT DOCUMENTS

| | | |
|---|---|---|
| EP | 2414020 A1 | 2/2012 |
| JP | 1049571 A1 | 2/1989 |
| JP | S64-49571 A | 2/1989 |
| JP | 2005342470 A | 12/2005 |
| WO | WO-9519800 A1 | 7/1995 |
| WO | WO-0069359 A1 | 11/2000 |
| WO | WO 2007/079014 A2 | 7/2007 |
| WO | WO 2007/121131 A2 | 10/2007 |
| WO | WO 2008/024597 A2 | 2/2008 |
| WO | 2010114800 A1 | 10/2010 |

OTHER PUBLICATIONS

PCT/US2008/053460 filed Feb. 8, 2008 International Preliminary Report on Patentability dated Aug. 11, 2009.
PCT/US2010/029089 filed Mar. 29, 2010 Search Report dated May 20, 2010.
PCT/US2010/029089 filed Mar. 29, 2010 Written Opinion dated May 20, 2010.
CN 20080004398.9 filed Feb. 8, 2008 First Office Action dated Dec. 23, 2011.
JP 2009-549266 filed Feb. 8, 2008 Office Action dated Apr. 10, 2012.
CN 20080004398.9 filed Feb. 8, 2008 Second Office Action dated Oct. 8, 2012.

* cited by examiner

SHAPE MEMORY MEDICAL DEVICE AND METHODS OF USE

CROSS-REFERENCE TO RELATED APPLICATION

This application claims the benefit of the U.S. Provisional Patent Application No. 60/900,202, filed Feb. 8, 2007, and entitled "Shape Memory Medical Device and Methods of Use," which is incorporated herein by reference in its entirety.

TECHNOLOGY FIELD

The present invention generally relates to medical devices. In particular, embodiments of the present invention relate to a medical device, such as a guidewire, having a shaped proximal end to assist in the intravascular placement of various apparatus.

BRIEF SUMMARY

Guidewires are commonly employed to assist in placing medical apparatus intravascularly within a patient. One material commonly employed in forming guidewires is nitinol, an alloy containing both nickel and titanium. Nitinol is preferred for many guidewires because it offers excellent kink resistance, a quality that eases guidewire advancement into the patient vasculature.

It is generally advantageous to prevent a guidewire from advancing into the patient vasculature further than is desired. If not properly secured by a clinician during patient insertion, however, the guidewire may be inadvertently and undesirably pulled—by blood flow or other means—further into the vasculature. If the guidewire has been placed in its desired position prior to such inadvertent advancement, the clinician must then partially pull the guidewire out and position it anew, costing time and effort, and increasing the possibility of injury to the patient. A need therefore exists in the art to overcome these challenges.

The present invention has been developed in response to the above and other needs in the art. Briefly summarized, embodiments of the present invention are directed to a shaped guidewire for use in medical applications. The guidewire is shaped so as to prevent inadvertent advancement of the guidewire into the corpus of a patient during use.

In one embodiment, the guidewire includes an elongate body that defines proximal and distal ends. The guidewire body further defines a shaped portion that is positioned intermediate the proximal and distal ends. The shaped portion of the guidewire is at least partially composed of a shape memory material, such as nitinol, and is deflected from a longitudinal axis defined by an undeflected portion of the guidewire body.

The shaped portion is disposed in one embodiment at the proximal end of the guidewire so as to prevent the guidewire from undesirably advancing further into the vasculature of a patient during use. The shaped portion of the guidewire contacts the tissue or apparatus at the incision site of the patient, which causes the guidewire to cease further advancement. Various shaped configurations for the shaped portion are possible including semi-circular and geometric shapes.

In another embodiment, a proximal portion of the nitinol guidewire can be treated to impart malleability and enable deflection by a clinician. In this way, various devices such as needles, introducers, etc., can be fed over the proximal end of the guidewire before the shaped portion is formed. Methods for forming the shaped or malleable guidewire to include a deflected portion are also disclosed.

In yet another example embodiment, the guidewire can be composed of distinct materials according to guidewire region. For example, a proximal segment of the guidewire can include stainless steel while a distal segment includes nitinol. A guidewire so configured can be easily deflected and shaped at the proximal end due to its formation from stainless steel, while the nitinol distal segment retains desired kink-resistant qualities. The two segments can be joined together by welding or other suitable process.

These and other features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof that are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF SELECTED EMBODIMENTS

Reference will now be made to figures wherein like structures will be provided with like reference designations. It is understood that the drawings are diagrammatic and schematic representations of exemplary embodiments of the invention, and are not limiting of the present invention nor are they necessarily drawn to scale.

FIGS. 1-7 depict various features of embodiments of the present invention, which is generally directed to a guidewire for use in medical applications. The guidewire as disclosed herein includes a proximal portion that is deflected from the axis of the remainder of the guidewire so as to prevent inadvertent advancement of the guidewire into the corpus of a patient during use. In one embodiment, the guidewire is at least partially composed of a shape memory material, such as nitinol. Methods for forming the guidewire so as to include a deflected proximal portion are also disclosed.

Figure 1:
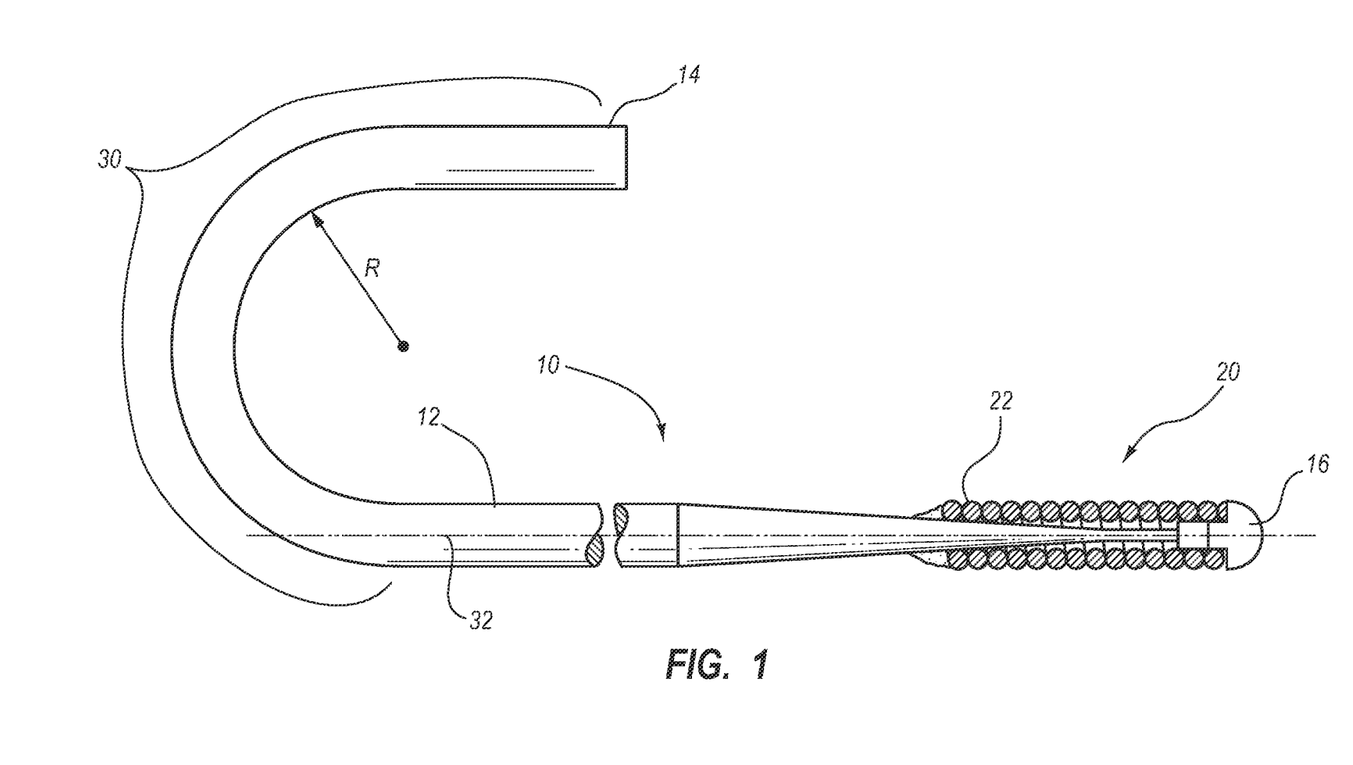
FIG. 1 is a side view of a guidewire configured in accordance with one example embodiment of the present invention.

Reference is first made to FIG. 1, which shows a guidewire, generally designated at 10, configured according to one example embodiment. As shown, the guidewire 10 includes an elongate body 12 defining both a proximal end 14 and a distal end 16. In this embodiment, a tip portion 20 is included near the distal end 16 and includes a coil 22 wrapped about the body 12. The coil 22 assists in providing atraumatic advancement of the guidewire 10 through the vasculature of a patient, via a percutaneous slit. Note that, once disposed in a vessel of the patient, the coil 22 of the tip portion 20 can obstruct the flow of fluids, such as blood, circulating in the vessel. As such, the interaction of the fluid with coil 22 can impart a distally directed force on the guidewire 10, tending to undesirably advance the tip portion 20 deeper into the vasculature. Embodiments of the present invention are intended to prevent such an occurrence. Note that in other embodiments the tip portion at the guidewire body distal end can include other configurations, such as a "J"-tip that facilitates advancement of the guidewire through tortuous paths in the patient vasculature without piercing the vessel wall.

In accordance with the present embodiment, the guidewire further includes a shaped proximal portion ("shaped portion"), generally designated at 30. As shown, the shaped portion 30 is located proximate the proximal end 14 of the guidewire 10. The shaped portion 30 is configured so as to prevent unintended advancement of the guidewire 10 into the vasculature of the patient during use. In the illustrated embodiment, the shaped portion 30 is shown deflected from a longitudinal axis 32 in a semi-circular bend having a radius R. As shown and discussed below, however, the shaped portion can have one of a variety of shapes.

Figure 2:
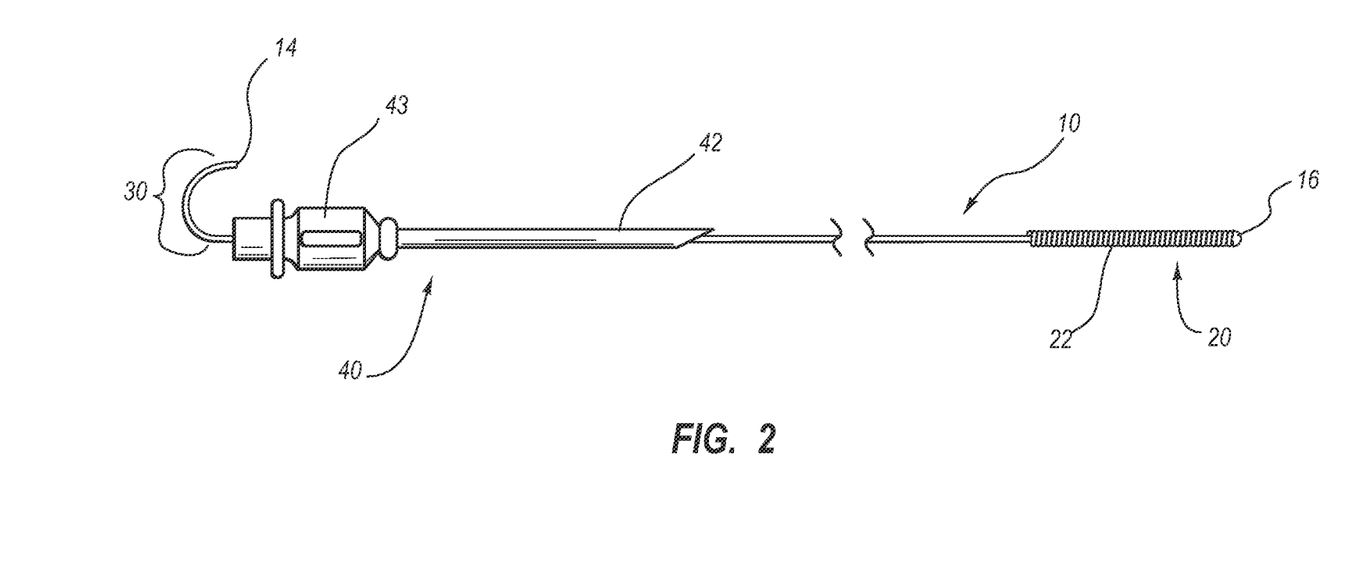
FIG. 2 is a side view showing the guidewire of FIG. 1 received through a needle assembly.

Together with FIG. 1, reference is now made to FIG. 2, which shows the guidewire 10 received in operable engagement with a needle assembly 40. Such a needle assembly 42 may be used in one embodiment to introduce the guidewire 10 into the vasculature of a patient. As shown, the guidewire 10 passes through both a needle 42 of the needle assembly 40 and a luer fitting 43 attached thereto. The shaped portion 30 of the guidewire 10, however, is sized and configured so as not to pass through the luer fitting 43, thereby preventing advancement of the guidewire 10 into the vasculature past a certain point. In other applications, the shaped portion will interact with a portion of another device, such as an introducer, or with the tissue of the patient proximate the incision, to inhibit further guidewire advancement.

Note that the shaped portion 30 of the guidewire 10 in one embodiment is somewhat flexible so as to enable medical devices, such as needles, introducers, and the like to be slid over the guidewire from the proximal end 14. Nonetheless, the shaped portion 30 is sufficiently stiff so as to return to its deflected state once any deforming load is removed therefrom.

In accordance with one embodiment, the shaped portion 30 of the guidewire 10 is composed of a shape memory material, including shape memory alloys, ferromagnetic shape memory materials, shape memory polymers, and the like. A "shape memory material" is understood herein to mean a material that can return to some previously defined shape after deformation, i.e., it "remembers" its geometry when subjected to an appropriate thermal procedure (a "one-way effect") or after a deforming load is removed therefrom, typically at higher ambient temperatures ("superelasticity").

One example of a shape memory material is nitinol, an alloy including, in one implementation, about 55-56% nickel and 44-45% titanium. In one embodiment, the shaped portion 30 includes nitinol. As mentioned above, nitinol can be employed as an excellent guidewire material for its kink-resistant properties. However, forming a bent or shaped portion in a nitinol guidewire has been difficult due to its shape memory properties. As will be disclosed, embodiments of the present invention contemplate forming such a bent portion, such as the shaped portion 30 shown in FIGS. 1 and 2, in a nitinol guidewire. Note that the shaped portion 30 may be composed entirely or partially of nitinol, or the entire guidewire 10 may include nitinol. Additionally, the relative concentrations of nickel and titanium in the nitinol material may vary from what is explicitly described herein.

In one embodiment the guidewire 10 has a diameter in the range of from about 0.018 to 0.038 inch and a length in a range of from about 35 to 180 centimeters, though other diameters and lengths are, of course, possible.

By way of example, shape memory materials can include alloys such as copper-zinc-aluminum alloys, copper-aluminum-nickel alloys, and nickel-titanium alloys. The shape memory properties of shape memory alloys are due to a temperature-dependent martensite phase transformation from a low-symmetry to a highly symmetric crystallographic structure. Those crystal structures are known as martensite and austenite. The temperatures at which a shape memory alloy changes its crystallographic structure are characteristic of the alloy and can be tuned by varying the elemental ratios. $A_s$ and $A_f$ are referred to as the temperatures at which the reverse transformation from martensite to austenite start and finish, respectively. By way of example, $A_s$ (austenite start), in some materials, varies between approximately −150 degrees Celsius to 200 degrees Celsius and $A_f$ (austenite finish) can range from changes in temperature from two to greater than 20 degrees Celsius.

Many shape memory alloys exhibit both shape memory and superelastic behavior. Alloy composition and the material's thermo-mechanical processing history dictate the temperatures where these properties exist. Superelasticity occurs when a shape memory alloy is mechanically deformed at a temperature above its $A_f$ temperature. This deformation causes a stress-induced phase transformation from austenite to martensite. The stress-induced martensite is unstable at temperatures above its $A_f$ so that when the stress is removed the material will immediately spring back or return to the austenite phase and its pre-stressed position. For reference, a graph 300, showing a phase transformation hysteresis curve 310, is included in FIG. 6.

In one embodiment, a guidewire having a proximal portion composed at least partially of nitinol can be processed by a "shape set annealing" process to define the shaped portion 30 as seen in FIGS. 1 and 2. To do so, the portion of the guidewire 10 proximate the proximal end 14 is deformed to a desired shape, then constrained to remain in the desired shape. This may be accomplished by a mandrel or other suitable device. The guidewire portion is then heat treated. Though actual temperatures and heating times vary according to the particular composition and characteristics of the portion being shaped, in one embodiment, the guidewire portion is heated to 500-550 degrees Celsius, followed by a rapid cooling, including for instance a water quench of the guidewire portion. In addition to maintaining the superelastic and shape memory properties, this process will impart to the guidewire portion a desired shape, such as the semi-circular configuration of the shaped portion 30 of the guidewire 10 shown in FIGS. 1 and 2.

Figure 3:
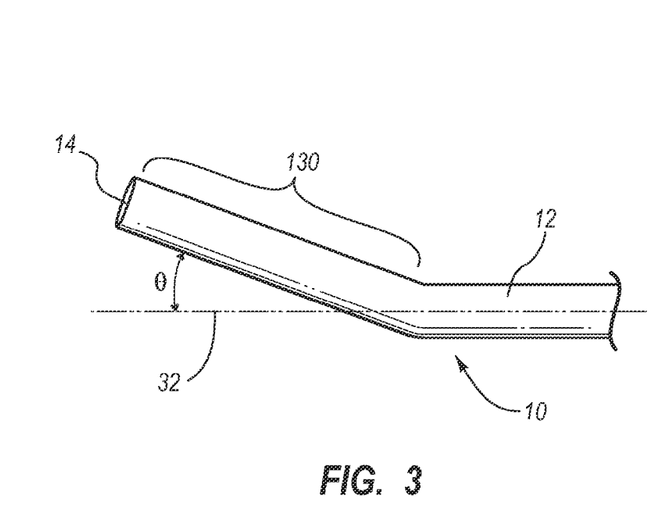
FIG. 3 is a side view showing a proximal portion of a guidewire configured according to another example embodiment.
Figure 4:
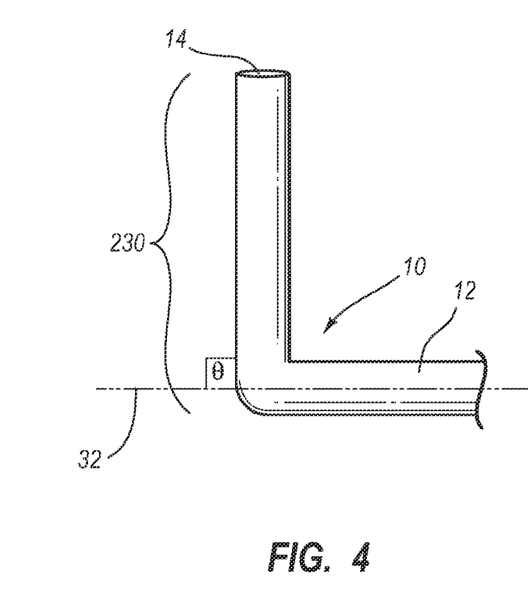
FIG. 4 is a side view showing a proximal portion of a guidewire configured according to yet another example embodiment.
Figure 5:
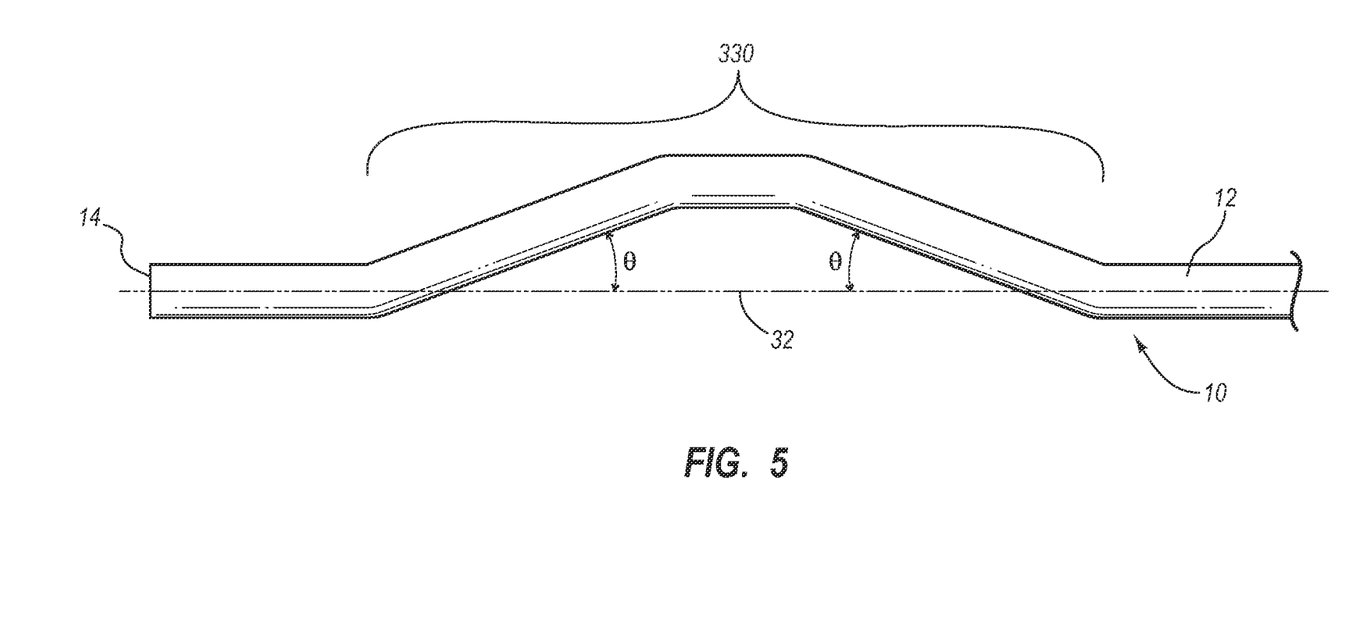
FIG. 5 is a side view showing a proximal portion of a guidewire configured according to still another example embodiment.
Figure 6:
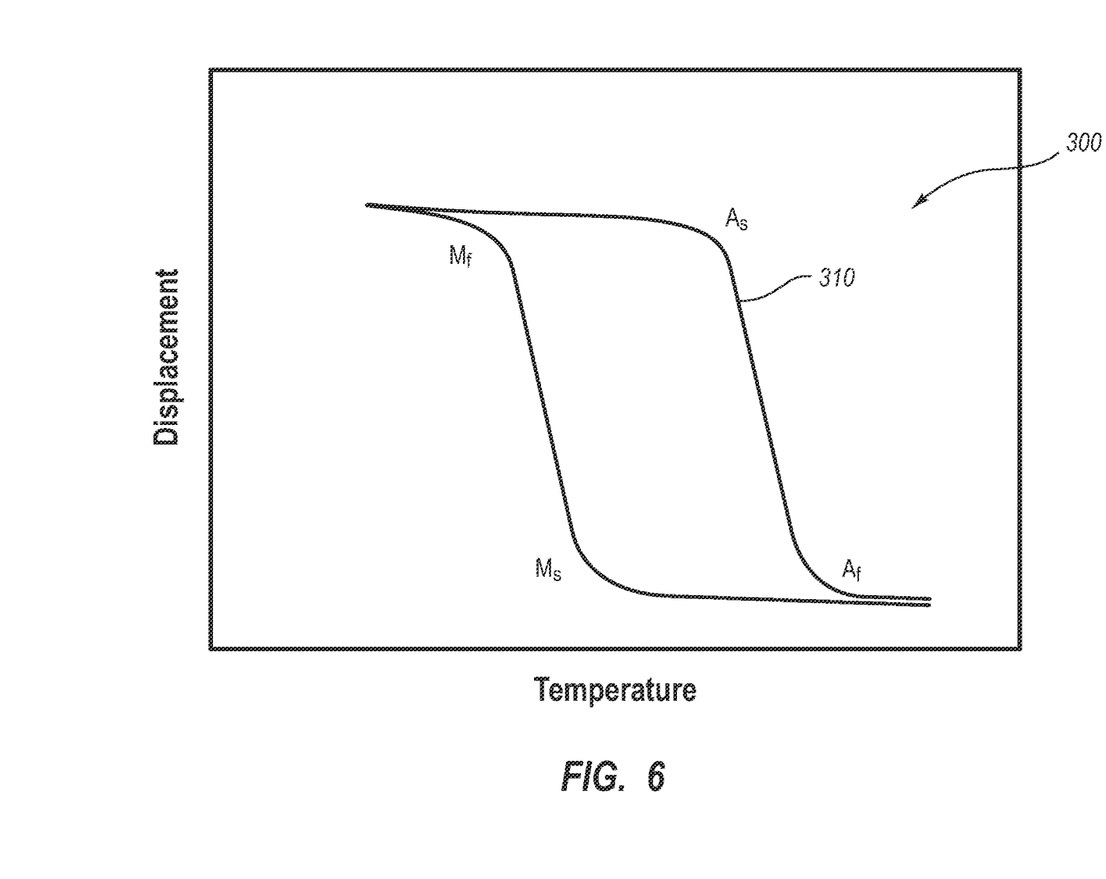
FIG. 6 is a graph showing a typical transition hysteresis curve of nitinol material.

The shaped portion 30 represents only one example of a variety of shapes and deflections that can be formed on a nitinol guidewire. FIGS. 3-5 depict various examples of this principle. Specifically, FIG. 3 shows a proximal shaped portion 130 on a guidewire 10 that is bent with respect to the longitudinal axis 32 of the undeflected portion of the guidewire body 12. The shaped portion 130 is deflected so as to define an angle 0 with the axis 32. FIG. 4 shows a proximal shaped portion 230 that defines a right angle 0 with the axis 32 of the guidewire body 12. FIG. 5 depicts yet another example of a deflection, wherein a portion of the guidewire 10 intermediate the guidewire proximal end 14 and distal end 16 is geometrically shaped to resemble a plateau, thus defining a shaped intermediate portion 330. It is therefore appreciated that the shaped portion can be positioned proximate the proximal guidewire end, or in some other intermediate location along the guidewire. It is further appreciated that the shaped portion can be shaped any one of a variety of ways, such as hook-shaped, circular, semi-circular, square, or other geometric or angled shapes or portions thereof.

In yet another embodiment, a portion of the guidewire manufactured from nitinol or other suitable shape memory material is subjected to heat treatment (e.g., annealing) without first deflecting the portion. By treating it in this manner at a desired temperature, the guidewire portion loses its superelastic characteristics and becomes malleable. Later, when the clinician advances the guidewire into the patient vasculature, the distal portion of the guidewire retains its kink-resistant qualities while the heat-treated portion is malleable. This allows the clinician to bend the guidewire portion, such as the proximal portion, to form a hook or other angled member to prevent migration of the guidewire 10 into the vasculature of the patient. In one possible implementation, the clinician can advance a needle, or other medical apparatus (e.g., vessel dilator, catheter), over the guidewire before bending the proximal portion of the guidewire. In one example embodiment, a 10 cm proximal portion of a nitinol guidewire having a total length of about 50 cm is heat treated so as to be malleable. The remaining 40 cm of the guidewire is left untreated so as to retain preferred kink-resistant qualities. The lengths of the various portions described above are variable according to need for a particular application.

The proximal portion of the guidewire in this embodiment is subject to heat treatment from about thirty seconds to about fifteen minutes at temperatures ranging from about 200 to about 450 degrees Celsius. The guidewire can be heat treated in a conventional oven, an IR oven, by laser, or by any other suitable method. In one aspect, following heat treatment, the guidewire is subjected to a water bath. Note that the temperature and time parameters specified above can vary according to a particular application.

Figure 7:
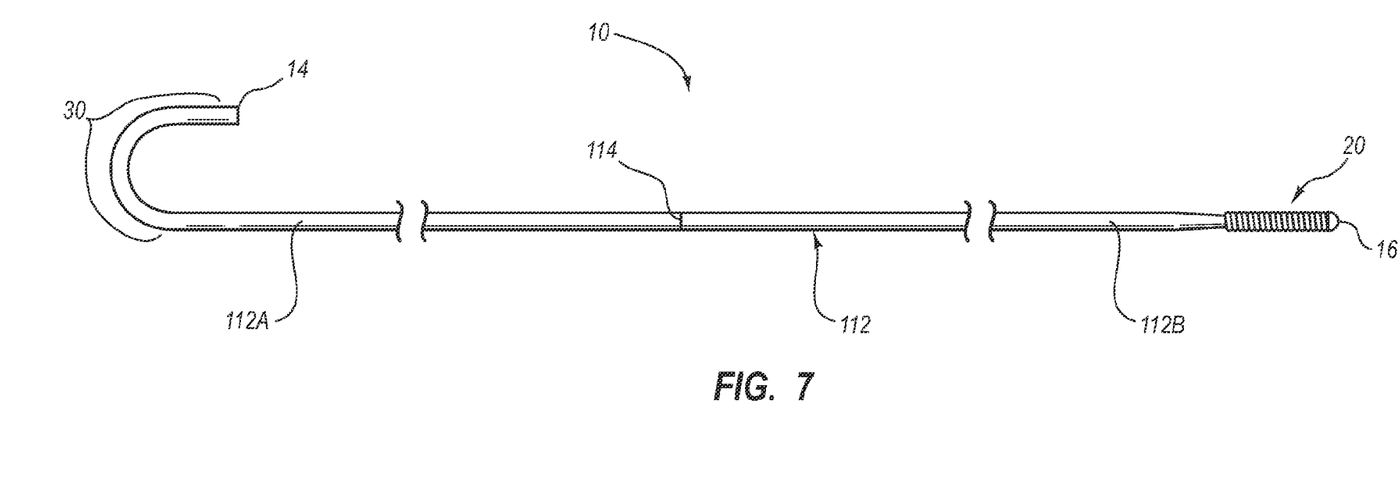
FIG. 7 is a side view of a guidewire configured according to an example embodiment of the present invention.

In another example embodiment, the guidewire can be composed of distinct materials according to guidewire region. This is shown in FIG. 7, wherein the guidewire 10 includes a body 112. The guidewire body 112 includes a proximal segment 112A and a distal segment 112B. The proximal segment 112A, representing a portion of the guidewire body 112 extending from the proximal end 14 and including the shaped portion 30, includes stainless steel, thus giving the proximal portion bendability in order to form the shaped portion.

In contrast, the distal segment 112B extending from the distal end 16, includes nitinol, which gives the distal segment preferred kink-resistant qualities. The proximal and distal segments 112A and 112B can be joined by any suitable process, including bonding, welding, and the like. The relative portion of the guidewire 10 that is defined by the proximal and distal segments 112A and 112B can vary according to the particular application. Further, note that other materials in addition or alternative to stainless steel and nitinol can be included in the respective guidewire segments.

Note that, while the discussion above has focused on guidewires, in other embodiments the principles of the present invention can be applied to other medical apparatus, including for example a stiffening member for use with intravenous catheters. Also, the length of the shaped guidewire portion can vary according to the particular needs of an application.

The present invention may be embodied in other specific forms without departing from its spirit or essential characteristics. The described embodiments are to be considered in all respects only as illustrative, not restrictive. The scope of the invention is, therefore, indicated by the appended claims rather than by the foregoing description. All changes that come within the meaning and range of equivalency of the claims are to be embraced within their scope.

What is claimed is:

1. A guidewire system, comprising:
   a shapeable guidewire having an elongate body defining proximal and distal ends aligned along a longitudinal axis of the elongate body, the body including:
      a shapeable portion, wherein the shapeable portion:
         is at least partially composed of a shape memory material,
         is deflectable from the longitudinal axis of the body, and
         is malleable so as to be shaped by a user before, during, or after use of the guidewire; and
   an apparatus that can be positioned at an incision site on a corpus of a patient to interact in contact with the shapeable portion of the elongate body to prevent further advancement of the guidewire into a vasculature of the patient.

2. The guidewire system as defined in claim 1, wherein the shape memory material is a shape memory alloy.

3. The guidewire system as defined in claim 2, wherein the shape memory alloy includes nickel and titanium.

4. The guidewire system as defined in claim 3, wherein the shapeable memory alloy includes nitinol.

5. The guidewire system as defined in claim 1, wherein the shapeable portion includes a segment that is deflected an angle greater than zero with respect to the longitudinal axis.

6. The guidewire system as defined in claim 1, wherein the shapeable portion is disposed at the proximal end of the guidewire body.

7. The guidewire system as defined in claim 6, wherein the shapeable portion defines a semi-circular shape.

8. A method for forming a guidewire, the method comprising:
   defining an elongate body of the guidewire including a proximal end and a distal end aligned along a longitudinal axis of the elongate body, a proximal portion of the body located proximate the proximal end including a shape memory material having superelastic characteristics;
   heat-treating the proximal portion such that the proximal portion loses the superelastic characteristics and becomes malleable and bendable into multiple shapes by a user of the guidewire and remains malleable and bendable after cooling; and
   cooling the proximal portion.

9. The method for forming as defined in claim 8, wherein heat-treating the proximal portion is done without deflecting the proximal portion from the longitudinal axis.

10. The method for forming as defined in claim 8, wherein heat treating the proximal portion further comprises:
    heat treating the proximal portion for a time in a range of from about 30 seconds to about 15 minutes.

11. The method for forming as defined in claim 8, wherein heat treating the proximal portion further comprises:

heat treating the proximal portion at a temperature in a range of from about 200 to about 395 degrees Celsius.

12. The method for forming as defined in claim 8, wherein cooling the proximal portion further comprises:
cooling the proximal portion in a water bath.

13. The method for forming as defined in claim 8, wherein the entire guidewire body includes nitinol, and wherein a distal portion of the guidewire body is not heat treated.

14. A shaped guidewire, comprising:
an elongate body, including:
a distal segment including nitinol; and
a proximal segment including stainless steel, the proximal segment including a shaped portion that is deflected from a longitudinal axis defined by an undeflected portion of the proximal segment, the shaped portion configured to prevent unintended advancement of the guidewire into a vasculature of a patient past the shaped portion when the shaped portion is in contact with tissue of a patient or an apparatus at an incision site.

15. The shaped guidewire as defined in claim 14, wherein the shaped portion is semi-circularly shaped.

16. The shaped guidewire as defined in claim 14, wherein the proximal and distal segments are joined to one another via welding.

17. The shaped guidewire as defined in claim 14, wherein the distal segment is relatively more resistant to kinks than the proximal segment.

18. A shaped guidewire, comprising:
an elongate body defining proximal and distal ends aligned along a longitudinal axis of the elongate body, the body including:
a shaped portion at least partially composed of a shape memory material positioned intermediate the proximal and distal ends and deflected from the longitudinal axis of the body, the shaped portion configured to interact with tissue of a patient proximate an incision site on a corpus of the patient to prevent advancement of the guidewire into a vasculature of the patient past the shaped portion.

19. The shaped guidewire as defined in claim 18, wherein the shaped portion is substantially deformable when a load is applied thereon, and wherein the shaped portion returns to its undeformed shape when the load is removed.

20. The shaped guidewire as defined in claim 18, wherein the shaped portion is also configured to interact with an apparatus positioned at the incision site to prevent advancement of the guidewire into a vasculature of the patient past the shaped potion.

* * * * *